United States Patent [19]

Shieh

[11] 3,992,262

[45] Nov. 16, 1976

[54] MEDIA CONTAINING MOLASSES AND CORN STEEP LIQUOR FOR PRODUCING GLUCOSE ISOMERASE FROM ACTINOPLANES AND METHOD

[75] Inventor: Kenneth K. Shieh, St. Louis County, Mo.

[73] Assignee: Anheuser-Busch, Incorporated, St. Louis, Mo.

[22] Filed: Feb. 10, 1975

[21] Appl. No.: 548,537

[52] U.S. Cl. .............................. 195/66 R; 195/31 F; 195/62; 195/100
[51] Int. Cl.² .................. C12D 13/10; C12B 3/04
[58] Field of Search ............... 195/31 F, 66 R, 100, 195/62, 101, 102, 65, 96

[56] References Cited
UNITED STATES PATENTS 3,813,320  5/1974  Shieh et al. ..................... 195/66 R
3,834,988  9/1974  Shieh et al. ..................... 195/66 R

OTHER PUBLICATIONS

Tsumura et al., "Cultivation Methods for Aerobacter Cloacae", Shokuryo Kenkyusho Kenkyo Hokoku, No. 19, pp. 189–193 (1965).
Takasaki, "Glucose Isomerase", Chemical Abstracts vol. 79, Abs. No. 135314g, p. 241, (1973).

Primary Examiner—Louis Monacell
Assistant Examiner—Thomas G. Wiseman
Attorney, Agent, or Firm—Gravely, Lieder & Woodruff

[57] ABSTRACT

This disclosure relates to an improved medium for growing organisms (preferably Actinoplanes missouriensis) which produce glucose isomerase. Use of the medium results in increased yields of enzyme in shorter fermentation times. The improved medium contains molasses, corn steep liquor, and an inorganic nitrogen salt.

5 Claims, No Drawings

MEDIA CONTAINING MOLASSES AND CORN STEEP LIQUOR FOR PRODUCING GLUCOSE ISOMERASE FROM ACTINOPLANES AND METHOD

BACKGROUND OF THE INVENTION

In U.S. Pat. Nos. 3,813,320 and 3,834,988 (of which the applicant herein is a co-inventor), there are shown various media and various microorganisms which produce glucose isomerase. U.S. Pat. No. 3,813,320 involves the use of *Aerobacter levanicum* in a two-stage fermentation procedure using unpurified hardwood sulfite liquor as part of the medium in the second stage where the glucose isomerizing enzyme is produced. U.S. Pat. No. 3,834,988 shows the production of glucose isomerizing enzymes from an organism of the Actinoplanes genus in a medium whose principal constituent is corn steep liquor which has had the sludge removed. In the patent and scientific literature there are disclosures of other microorganisms which produce glucose isomerizing enzymes. Some of these enzymes convert D-glucose to D-fructose through one or more chemical intermediates (e.g., D-glucose-6-phosphate) but these enzymes do not appear to be practical for industrial use at the present time.

More promising are enzymes known as glucose isomerase that convert D-glucose to D-fructose directly. A number of these enzymes have been prepared from microorganisms of the genera lactobacillus, Pseudomonas, Pasteurella, Leuconostoc, Streptomyces and Aerobacter (see review by Yamanaka in Biochem. Biophys. Acta 151, 670–680). In order that a significant quantity of glucose isomerase be formed by any of the foregoing microorganisms, xylose or xylan must be present in the growth medium to induce the enzyme. Pure xylose is relatively expensive, and when xylan is used in the growth medium, the microorganism must also produce enzymes capable of hydrolyzing the xylan.

In order to overcome the expense of growing the microorganism in a xylose or xylan-containing medium, efforts have been expended to obtain a bacterium that will produce the enzyme constitutively. Lee, Hayes and Long (U.S. Pat. No. 3,645,848) have disclosed that certain strains of microorganisms belonging to the genus Arthrobacter are capable of producing enzymes that directly convert glucose or xylose to the corresponding ketose when grown in a medium from which xylose or xylan is absent. Relatively small amounts of isomerase are produced and the growth medium requires relatively expensive nitrogen sources, such as yeast extract and meat protein.

SUMMARY OF THE INVENTION

Accordingly, one of the principal objects of the present invention is to provide a method of growing microorganisms possessing enzymes for converting aldoses to ketoses using a medium which is relatively inexpensive and which results in good yields of enzyme.

This invention comprises a method of producing glucose isomerizing enzyme in a medium comprising molasses, corn steep liquor (preferably filtered to remove the sludge) and an inorganic nitrogen salt.

DETAILED DESCRIPTION

I have discovered that microorganisms which produce glucose isomerase are capable of being grown in large numbers on a medium of which the principal ingredients are beet molasses, corn steep liquor, and an inorganic nitrogen salt.

The preferred microorganism is of the genus Actinoplanes, but other glucose isomerizing organisms of the genera Lactobacillus, Pseudomonas, Pasteurella, Leuconostoc, Streptomyces, Aerobacter, Arthrobacter, Bacillus, Nocardia, Micromonospora, Microbiospora, Microellobospora, Thermoactinomyces, Thermopolyspora, Thermomonospora and Pseudonocardia can be grown on this medium.

GROWTH OF SEED INOCULUM

A seed inoculum of Actinoplanes missouriensis NRRL B-3342 is grown up by shaking at 28° C. for 24 hours in a 1-liter Erlenmeyer flask containing 400 ml. of inoculum media which consists of 0.25% glucose, 0.25% dipotassium phosphate, 0.8% Tryptone (Difco), 0.2% Soytone (Difco) and 1% casein hydrolyzate (Amber).

The seed inoculum also can be grown according to the procedure set forth in U.S. Pat. No. 3,834,988.

The seed inoculum is added to a growth medium which contains molasses, corn steep liquor from which the sludge has been removed, an inorganic nitrogen salt, other salts, water, and an anti-foaming agent. The medium is at a pH of about 7.

The molasses can be cane molasses, beet molasses, or mixtures of cane and beet molasses, but beet molasses is preferred.

MEDIUM COMPOSITION

The medium can contain 2% to 8% beet molasses, about 0.6% to 4% corn steep liquor, and 0.1% to 0.6% sodium nitrate. The remainder of the medium is water.

A specific preferred medium composition is composed of 3% beet molasses, 1% corn steep liquor, 0.2% $NaNO_3$, 0.025% $MgSO_4 \cdot 7 H_2O$, 0.1% $K_2HPO_4$, 0.025% KCl, 0.001% $FeSO_4 \cdot 7 H_2O$, and 0.06% Dow Corning Antifoam A (10% solid). The sludge of corn steep liquor is first removed by filtration or centrifugation after mixing with molasses and adjusting the pH to 7.1 with NaOH. The corn steep liquor can be filtered alone. Other solids are added to compensate for variations in the compositions of the products which are the main constituents of the medium.

The fermenter is sterilized for 60 minutes at 121° C. Growth is started by adding 4% inoculum to the medium in the fermentation. Aeration and agitation are set at 8 liters per minute or 0.8 vvm and 200–300 rpm, respectively. Temperature is set at 28° C.

DETERMINATION OF GLUCOSE ISOMERASE ACTIVITY

The cells are collected by centrifuging 30 ml. of the culture at 10,000 x g for 10 minutes. The cells are washed once with tap water, and sonified at 4° C. for 4 minutes in a Branson Sonifier J-17A after suspending in 14 ml. of 0.12 M phosphate buffer (pH 7.0). The cell-free extract is obtained by centrifugation at 27,000 x g for 15 minutes and used as a source of glucose isomerizing enzyme.

The activity of glucose isomerase is determined as follows: to 3.0 ml. of assay solutions composed of 2.0 M glucose, 0.004 M $MgSO_4$ and 0.0004 M $CoSO_4$ is added a crude enzyme solution in 0.12 M phosphate buffer of pH 7.0 to a final volume of 4.0 ml. The reaction is carried out at 75° C. Aliquots are taken at 10, 15, 20 and 25 minutes and diluted in 0.02 M HCl.

The fructose content of the samples is assayed in an automatic analyzer by adapting the skatole-HCl method described by Pogell. The color development is carried out at 52° C. as opposed to 37° C. Activity of glucose isomerizing enzyme is calculated from the slope and expressed in units (u). A unit of activity is defined as that quantity of enzyme which will produce 1 micromole of fructose from the glucose in 1 minute at 75° C.

Following in Table I is a comparison of the production of glucose isomerase cells from this medium which contains beet molasses and corn steep liquor with a medium containing only corn steep liquor. From Table I, it is apparent that BM-CSL medium is superior to CSL medium with respect to the production of glucose isomerase by the said organism.

TABLE I

Comparison of Glucose Isomerase Production Between Cells Growing in Corn Steep Liquor Medium (CSL) and Cells Growing in Beet Molasses-Corn Steep Liquor Medium (BM-CSL).

| Growth Periods (hr.) | Production of Enzyme ($\mu$/ml. culture)* | |
|---|---|---|
| | Cells Grown in CSL Medium** | Cells Grown in BM-CSL Medium |
| 24 | 2.5 | 9.6 |
| 36 | — | 23.2 |
| 48 | 8.7 | 39.0 |
| 60 | 16.7 | 50.5 |
| 72 | 20.9 | 51.0 |

*pH of cultures was not controlled
**CSL medium contained 4% corn steep liquor supplemented with 0.1 mM Co++ and 0.05 mM Cu++

Table II which follows shows that removal of sludges from corn steep liquor is essential to the production of glucose isomerase from *Actinoplanes missouriensis*. It also shows that a molasses medium will support growth of the organism to produce glucose isomerase, but that the combination of molasses and corn steep liquor greatly increases the production of isomerase.

TABLE II

Effect Of Corn Steep Liquor Sludge On The Production Of Glucose Isomerase From *Actinoplanes Missouriensis* (Shaker Grown Cells)

| Media | Production of Enzyme ($\mu$/ml.) culture |
|---|---|
| Molasses medium (no corn steep liquor) | 17.9 |
| Molasses and corn steep liquor* (sludges have not been removed) | 0 (no growth) |
| Molasses and corn steep liquor* (sludges have been removed) | 32.0 |

*Molasses: 3.2%; Corn steep liquor: 1.0%. Grown for 4 days.

As mentioned, the optimal concentration of beet molasses for production of glucose isomerase is between about 2% to about 8%. The preferred concentration is about 3%. The production of enzyme decreases sharply in the presence of more than 10% molasses. Table III which follows demonstrates these data. The media contained 1.5% corn steep liquor except for Run 5. The amounts of beet molasses varied as indicated. The rest of the media were as set forth hereinbefore under 'Medium Composition'.

TABLE III

Effect of Beet Molasses Concentrations on the Production of Glucose Isomerase

| Growth Periods hrs. | Enzyme Production and Growth | % Beet Molasses In Each Fermentation Run[1] | | | | | | | | | |
|---|---|---|---|---|---|---|---|---|---|---|---|
| | | Run-1 0 | Run-2 1.0 | Run-3 2.0 | Run-4 3.0 | Run-5 3.0 | Run-6 4.0 | Run-7 5.0 | Run-8 6.0 | Run-9 8.0 | Run-10 10.0 |
| 24 | Activity[2] | ND[4] | ND | ND | 11.0 | 7.1 | 15.4 | 12.2 | 7.8 | 16.9 | ND |
| | Growth[3] | ND | ND | ND | 1.3 | 0.6 | 1.6 | 1.5 | 1.0 | 1.2 | ND |
| 36 | Activity | ND | ND | 9.8 | 33.3 | 15.1 | — | 24.4 | 23.0 | 21.1 | 6.2 |
| | Growth | ND | ND | 1.1 | 3.1 | 1.4 | — | 2.6 | 2.1 | 2.3 | 0.8 |
| 48 | Activity | ND | ND | 26.7 | 47.3 | 24.1 | 35.7 | 35.9 | 27.4 | 32.2 | 9.2 |
| | Growth | ND | ND | 2.9 | 3.5 | 1.8 | 3.0 | 3.2 | 2.5 | 3.1 | 1.3 |
| 60 | Activity | ND | ND | 48.4 | 59.2 | 28.6 | 57.3 | 50.3 | 41.3 | 44.1 | 12.3 |
| | Growth | ND | ND | 3.6 | 3.7 | 2.3 | 3.8 | 4.2 | 3.6 | 3.6 | 1.6 |
| 72 | Activity | 15.1 | 19.6 | 56.7 | 63.8 | 25.8 | 66.5 | 68.2 | 45.8 | 50.9 | 14.0 |
| | Growth | 0.8 | 1.2 | 3.3 | 3.5 | 2.3 | 4.3 | 4.9 | 4.0 | 3.9 | 1.7 |
| 84 | Activity | — | — | 62.0 | — | 32.4 | 78.8 | 63.0 | 60.2 | 61.1 | 10.8 |
| | Growth | — | — | 3.0 | — | 2.5 | 4.4 | 5.10 | 4.20 | 4.2 | 1.7 |
| 96 | Activity | 16.3 | 33.4 | 69.2 | — | 31.4 | 74.1 | 59.0 | 62.2 | 62.9 | 13.9 |
| | Growth | 0.7 | 1.8 | 3.2 | — | 2.7 | 4.3 | 4.9 | 5.3 | 4.4 | 1.6 |

[1]All fermentation runs contained 1.5% corn steep liquor except Run-5 in which CSL was omitted.
[2]$\mu$/ml culture
[3]mg extractable protein/ml culture
[4]not determined due to poor growth Table III shows that in the absence of beet molasses, the production of enzyme in the 72 hour old culture is only 24% of that obtained from the medium containing 3% molasses but the specific activity of enzyme from both media are almost the same (see Run-1 and Run-4 in Table III). In the absence of corn steep liquor, the production of enzyme from the medium containing 3% molasses is only 41% of that containing 1.5% corn steep liquor in addition to 3% molasses, but the specific activity of the former enzyme preparation is only 62% of the latter (see Run-5 in Table II). This result indicates that the corn steep liquor promotes the production of enzyme, whereas molasses stimulates the growth of the organism. Combinations of both molasses and corn steep liquor therefore increase the yields of the enzyme.

The amount of corn steep liquor that can be used is from about 0.6% to about 4.0%. Above 4% the growth may be poor depending on the quality of corn steep liquor. It preferably is about 1.5% as shown in Table IV which follows:

TABLE IV

Effect Of Corn Steep Liquor (CSL) Concentration On The Production Of Glucose Isomerase In The Beet Molasses Medium*
(Fermentor Grown Cells 60 Hours Old)

| Concentration of CSL | Production of Enzyme (μ/ml. culture) |
|---|---|
| 0 | 28.6 |
| 0.6 | 29.0 |
| 1.0 | 44.0 |
| 1.5 | 59.5 |

*The composition of this medium has been described hereinbefore under 'Medium Composition'.

Cane molasses, beet molasses and mixtures of cane and beet molasses can be used to produce glucose isomerase. This is illustrated as follows:

*Actinoplanes missouriensis* is cultured in 100 ml. of medium of 3% cane molasses, 1.5% desludged corn steep liquor mixture at a pH of 7.1 supplemented with minerals as hereinbefore described. The culture is grown in 250 ml. Erlenmeyer flasks on a rotary shaker at 28° C. for 4 days. The enzyme yields are then determined. The results are set forth in Table V.

TABLE V

| Molasses | % | Enzyme Yields (μ/ml. culture) |
|---|---|---|
| Cane | 3% | 29.7 |
| Beet | 3% | 39.2 |
| Cane and beet | 1.5% each | 34.6 |

From the foregoing Table V, it is apparent that cane molasses can also be used to produce glucose isomerase.

Inorganic nitrogen salts, as well as urea, also are effective in increasing enzyme production by a factor of 48% to 128%. In preparing the following Table VI, *Actinoplanes missouriensis* is grown in 100 ml. of filtrate of 3% beet molasses, 1.5% corn steep liquor mixture (pH 7.1), supplemented with minerals as previously described. The filtrate is placed in 250 ml. Erlenmeyer flasks and sufficient amounts of inorganic nitrogen salts such as $NaNO_3$, $NH_4NO_3$, $(NH_4)_2SO_4$, $NH_4H_2PO_4$, $NaNO_2$, and urea are added to the medium to give a final concentration of 5.9 mM of nitrogen atom.

After sterilization, the medium is inoculated, the flasks are placed on a rotary shaker, and the organism is grown in the flasks for 4 days at 28° C.

If $NaNO_3$ is the nitrogen salt, from about 0.1% to about 0.6% is used. Other nitrate salts can be used which give equivalent amounts of nitrate. The other nitrogen salts are used in amounts effective to give nitrogen equivalent to that in from 0.1% to 0.6% $NaNO_3$.

TABLE VI

Effect Of Inorganic Nitrogen Salts And Urea On The Production Of Glucose Isomerase Of *Actinoplanes missouriensis*

| Inorganic Nitrogen Salts | Enzyme Production μ/ml. culture |
|---|---|
| None | 19.4 |
| $NaNO_3$ | 32.5 |
| $NaNO_2$ | 28.6 |
| $(NH_4)_2SO_4$ | 44.0 |
| $NH_4NO_3$ | 37.8 |
| $NH_4H_2PO_4$ | 34.7 |
| Urea | 33.3 |

What is claimed is:
1. A method of improving glucose isomerase production from Actinoplanes comprising the steps of adding an inoculum of said organism to a fermentor containing molasses in amount sufficient to stimulate the growth of said organism, corn steep liquor from which the sludge thereof has been removed and in amount sufficient to stimulate glucose isomerase production, and an additional source of nitrogen in amount sufficient to increase glucose isomerase production, said additional source of nitrogen being selected from the group consisting of urea and inorganic nitrogen salts, growing said inoculum for a period of time and at a temperature sufficient to produce a desired yield of glucose isomerase, and harvesting the glucose isomerase, said molasses being present in amount of about 1% to about 10%, said corn steep liquor being present in amount of about 0.6% to about 4%, and said additional source of nitrogen being present in amount to provide nitrogen equivalent to that contained in $NaNO_3$ in concentrations of about 0.1% to about 0.6% $NaNO_3$.

2. The process of claim 1 wherein the molasses is selected from the group consisting of beet molasses, cane molasses, and mixtures of the two.

3. The process of claim 1 wherein the organism is *Actinoplanes missouriensis* NRRL-B3342.

4. The process of claim 1 wherein the nitrogen salt is $(NH_4)_2SO_4$.

5. The process of claim 1 wherein the nitrogen salt is $NaNO_3$.

* * * * *